United States Patent [19]

Rudolph

[11] Patent Number: 5,538,000
[45] Date of Patent: Jul. 23, 1996

[54] AIRFLOW DELIVERY SYSTEM

[75] Inventor: Kevin A. Rudolph, Overland Park, Kans.

[73] Assignee: Hans Rudolph, Inc., Kansas City, Mo.

[21] Appl. No.: 385,094

[22] Filed: Feb. 6, 1995

[51] Int. Cl.$^6$ .................................................. A61M 16/00
[52] U.S. Cl. ............................. 128/205.25; 128/207.18; 128/201.22
[58] Field of Search ........................ 128/201.22, 201.23, 128/207.18, 207.13, 206.21, 205.25

[56] References Cited

U.S. PATENT DOCUMENTS

| | | | |
|---|---|---|---|
| 853,431 | 5/1907 | Allen | 128/207.18 |
| 1,081,745 | 12/1913 | Johnston et al. | 128/203.25 |
| 1,192,186 | 7/1916 | Greene | 128/207.13 |
| 1,288,647 | 12/1918 | Miller | 128/207.13 X |
| 2,931,358 | 4/1960 | Sheridan | 128/207.18 |
| 3,683,907 | 8/1972 | Cotabish | 128/201.22 X |
| 4,422,456 | 12/1983 | Tiep | 128/207.18 |
| 4,744,946 | 10/1988 | Ackerman et al. | 128/207.18 |
| 4,782,832 | 11/1988 | Trimble, et al. | 128/207.18 |
| 4,944,310 | 7/1990 | Sullivan | 128/848 |
| 5,134,995 | 8/1992 | Gruenke et al. | 128/204.23 |
| 5,259,373 | 11/1993 | Gruenke et al. | 128/204.23 |

FOREIGN PATENT DOCUMENTS

| | | | |
|---|---|---|---|
| 0549299 | 6/1993 | European Pat. Off. | 128/207.18 |
| 1124404 | 10/1956 | France | 128/207.18 |
| 701690 | 12/1940 | Germany | 128/207.13 |
| 27599 | of 1904 | United Kingdom | 128/207.13 |

OTHER PUBLICATIONS

Puritan Bennett–1993–1994 Hospital Accessories Catalog, p. 43.

*Primary Examiner*—Stephen Funk
*Assistant Examiner*—Eric P. Raciti
*Attorney, Agent, or Firm*—Litman, McMahon and Brown

[57] ABSTRACT

An improved airflow delivery system wherein a primary conduit extends from a source of a stream of breathable gas to a patient or wearer. The primary conduit is rotatably connected to a manifold positioned on the top of the wearer's head. The manifold distributes the stream of breathable gas through at least two secondary conduits extending on generally opposite sides of the wearer's head to an airflow entrance structure for directing airflow into the nostrils of a wearer. This airflow entrance structure is a nasal mask or alternatively a nasal puff assembly. The secondary conduits are preferably secured to or integrally formed with straps connecting the airflow entrance structure to the manifold and used for securing the device to a user's head.

20 Claims, 1 Drawing Sheet

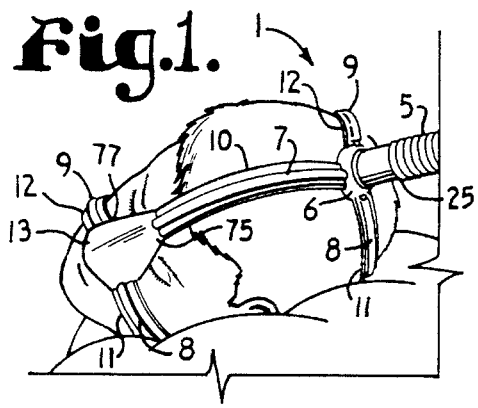
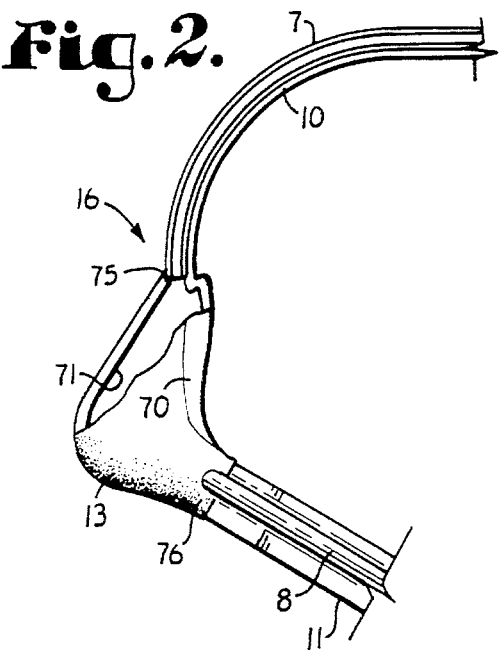
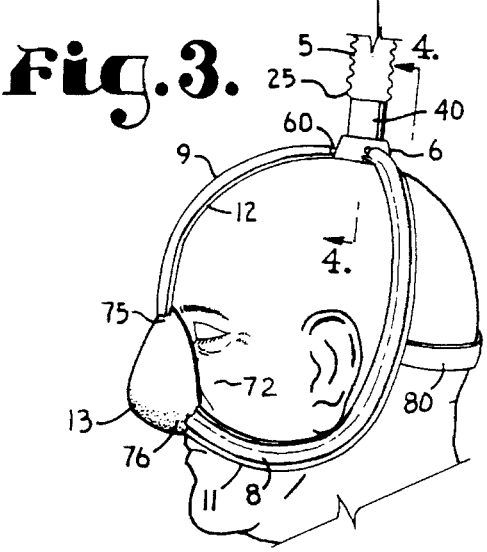
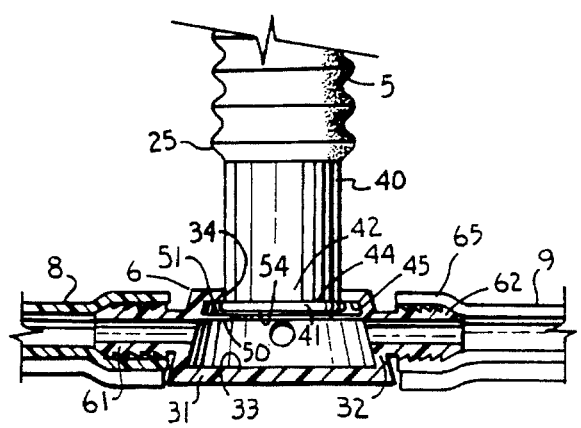

5,538,000

AIRFLOW DELIVERY SYSTEM

BACKGROUND OF THE INVENTION

The present invention relates to systems for delivering positive air pressure through the nasal passages to facilitate treatment of breathing disorders such as sleep apnea, ventilation difficulties or anesthetic gas administration.

Obstructive sleep apnea is caused by obstruction of the of the upper airway during sleep which results in the absence of airflow through the nose or mouth for at least 10 seconds. Obstructive sleep apnea episodes are usually most serve during periods of REM (Rapid Eye Movement) sleep, when muscle tone is inhibited. The upper airway then narrows as a result of the relaxation of a number of muscles. The suction pressure of inspiration then causes further narrowing or collapse of the airway. The lack of airflow causes the oxygen level in the blood to drop causing arousal which then restores upper airway muscle tone allowing normal breathing.

Heavy snoring and daytime sleepiness are the most common symptoms associated with obstructive sleep apnea syndrome. Other complaints include night-time thrashing, sleep walking, enuresis, disorientation, personality changes, intellectual deterioration, sexual dysfunction, hypnagogic hallucinations, automatic behavior and morning headaches. The prevalence of episodes of obstructive apnea and the frequency of occurrence increase with age. Men are much more commonly affected than women and nearly 50% of elderly men have 20 or more apneic episodes each night. Other known risk factors include obesity, chronic alcoholism, chronic obstructive pulmonary disease and postmenopausal state. Altogether more than 30,000 patients are treated each year for obstructive sleep apnea.

The most effective and frequently applied therapy for obstructive sleep apnea is by means of continuous positive airway pressure (CPAP). For such therapy, a patient is fitted with a tight fitting nasal mask connected through an airway to a blower which supplies air at a slight positive pressure to the nasal passages. The application of the slight positive pressure is immediately effective in reversing airway obstruction in most patients with obstructive sleep apnea. Although the therapeutic results of nasal CPAP are often dramatic and immediate, it is only effective when used properly and on a regular basis. Failure to apply nasal CPAP for even a single night results in recurrence of hypersomnolence the next day.

Problems associated with wearing existing masks or positive airway pressure delivery systems during periods of attempted sleep are sufficient to deter many patients from continuing CPAP therapy. Some problems include excessive noise resulting from leaks around improperly fitting masks or general discomfort caused by the design of the mask or the CPAP delivery system.

One conventional mask design includes an air delivery tubing of relatively large diameter connected to the front of a nasal mask through use of a swivel port. Such a tubing assembly is heavy and bulky making it extremely difficult to maintain a mask seal for airway pressure support with head movement during sleep. Any break in the mask seal results in air loss around the edges of the mask causing excessive noise and possibly reducing the positive pressure through the nasal passages to a level insufficient to prevent apneic events.

Another type of CPAP device replaces the mask with nasal prongs or pillows as shown in U.S. Pat. No. 4,782,832. In such a device, a large diameter air delivery tube is positioned in line with the nose across the top of the head and down the center of the forehead to connect to nasal pillows which are inserted in to the patient's nostrils. Placement of the large diameter air delivery tube on the head, makes the system uncomfortable and easy to dislodge with head movement during sleep which can result in displacement of the nasal pillows from the nostrils.

SUMMARY OF THE INVENTION

The present invention provides an improved airflow delivery system wherein a primary conduit extends from a source of a stream of breathable gas to a patient or wearer. The primary conduit is rotatably connected to a manifold positioned on the top of the wearer's head. The manifold distributes the stream of breathable gas through at least two secondary conduits extending on generally opposite sides of the wearer's head to an airflow entrance structure for directing airflow through the nostrils of a wearer and generally comprising a nasal mask or a nasal puff assembly.

The rotatable connection of the primary conduit to the manifold permits the primary conduit to remain in a generally fixed alignment as the wearer's head turns or rotates during sleep, thus reducing the likelihood of kinks or bends forming in the primary conduit and reducing stresses placed on the device including the airflow entrance structure thereby reducing the likelihood of displacement of the airflow entrance structure.

The incorporation of at least two secondary conduits flow connecting the manifold to the airflow entrance structure generally on opposite sides of the wearer's head, ensures that at least one such secondary conduit is always open when the wearer's head is turned so as to rest upon and compress the opposite secondary conduit.

The airflow entrance structure is secured to the manifold by a set of straps. The device includes at least two such straps preferably a left side strap and a right side strap. The left side strap generally extends from the left side of the airflow entrance structure to the left side of the manifold and is adapted to be positioned behind the left ear of the wearer. The right side strap generally extends from the right side of the airflow entrance structure to the right side of the manifold and is adapted to be positioned behind the right ear of the wearer. A front strap also preferably extends from an upper end of airflow entrance structure to a front end of the manifold.

The secondary conduits are preferably secured to and extend coextensively with the straps such that a frontal conduit is secured to the front strap and connected to the airflow entrance structure at an upper end thereof in flow communication with the airflow entrance structure, a left side conduit is secured to the left side strap and connected to the airflow entrance structure along a left side thereof in flow communication with the airflow entrance structure and a right side conduit is secured to the right side strap and connected to the airflow entrance structure along a right side thereof in flow communication with the airflow entrance structure.

OBJECTS AND ADVANTAGES OF THE INVENTION

Therefore it is an object of the invention to provide a device for directing the flow of gasses to or from a wearer; to provide such a device for providing a stream of breathable gas under a controlled pressure to a wearer; to provide such a device which may be easily secured to a wearer and which is relatively difficult to dislodge during use; to provide such a device which is relatively comfortable to wear; to provide such a device which permits relatively unrestricted movement of the head of a wearer during use; to provide such a device which provides continuous positive airway pressure to a patient; to provide such a device which is particularly well suited for use in the treatment of obstructive sleep apnea and related respiratory disorders and to provide such a device which is relatively easy and inexpensive to manufacture.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a fragmentary perspective view showing an airflow delivery system of the present invention secured to a head of a patient.

FIG. 2 is an enlarged and fragmentary left side elevational view of the airflow delivery system of the present invention with portions broken away to show interior detail thereof.

FIG. 3 is a fragmentary, partially schematic, left side elevational view of the airflow delivery system of the present invention secured to the head of a patient.

FIG. 4 is an enlarged and fragmentary cross-sectional view of the airflow delivery system, generally taken along line 4—4 of FIG. 3 with portions broken away to show interior detail thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 generally refers to the airflow delivery system of the present invention. The system 1 generally comprises a primary conduit 5, an airflow distributor or manifold 6, a frontal conduit 7, a left side conduit 8, a right side conduit 9, a frontal strap 10, a left side strap 11, a right side strap 12 and a nasal mask 13. The device is generally designed to deliver a stream of breathable gas under controlled pressure to the nasal passages of a patient, user or wearer. The airflow distributor 6, conduits 7, 8 and 9, straps 10, 11 and 12 and nasal mask 13 are collectively referred to as a headgear 16.

The primary conduit 5 is preferably formed of flexible plastic or rubber tubing and includes a first end (not shown) connected to a source of pressurized air 20 shown schematically in FIG. 3. A second end 25 of the primary conduit 5 is connected to the airflow distributor 6 in flow communication therewith in a manner which permits the primary conduit 5 to rotate or swivel with respect to the airflow distributor 6. As shown in FIG. 4, the airflow distributor 6 generally comprises an upper wall 30, a lower wall 31 and a circumferential side wall 32 which define an airflow distribution chamber 33.

A primary conduit receiving opening 34 extends through the upper wall 30 of the airflow distributor 6. The diameter of the opening 34 is slightly greater than the diameter of a sleeve 40 that is secured to the second end 25 of the primary conduit 5. The sleeve 40 includes a shoulder or lip 41 extending outwardly and circumferentially around the sleeve 40 at a distal end 42 thereof. The sleeve 40 is generally positioned within the primary conduit receiving opening 34 such that an upper surface 44 of the shoulder 41 engages an inner surface 45 of the airflow distributor upper wall 30. An inwardly projecting wall 50 extends inwardly from and circumferentially around the side wall 32. An upper surface 51 of the inwardly projecting wall 50 generally engages a lower surface 54 of the shoulder 41 in a manner sufficient to permit relatively free rotation of the sleeve 40 within the opening 34 while permitting a minimal amount of air leakage around the shoulder 41. It is foreseen that a wide range of structures could be used to permit rotational movement of the primary conduit 5 with respect to the airflow distributor 6 while minimizing the amount of air leakage through such structures. It is foreseen, for example, that the system could incorporate a swivel or ball type coupling between the primary conduit 5 and the airflow distributor 6.

Front, left side, and right side tube connectors 60, 61, and 62 respectively project outward from the side wall 32 of the airflow distributor 6 in flow communication with the chamber 33. The front, left side and right side conduits 7, 8 and 9 are connected at one end thereof to the front, left side and right side tube connectors 60, 61 and 62 respectively. The front, left side and right side conduits 7, 8 and 9 are collectively referred to as secondary conduits.

The nasal mask 13 is preferably constructed of silicone or other like material that is flexible yet resilient and that does not cause substantial skin irritation to the wearer. The mask 13 is adapted to form an airtight seal around the nose of a wearer through sealing means such as inwardly directed flexible flap 70 as shown in FIG. 2 which extends inwardly from the periphery of the mask 13 and conforms to seal about the face 72 of a wearer. The nasal mask 13 encloses the nose of a wearer and forms an airtight chamber 71 around the wearer's nose. The nasal mask 13 includes an upper end 75, a lower left side corner 76 and a lower right side corner 77.

The straps 10, 11 and 12 are preferably integrally formed with the nasal mask 13, but may be connected thereto by other means customary in the industry including adhesive means or buckles (not shown). The frontal, left side and right side conduits 7, 8 and 9 are also preferably integrally formed as a single unit with the frontal, left side and right side straps 10, 11 and 12 respectively, so that the straps 10, 11 and 12 operably help support, position and increase the compression strength of the respective conduits 7, 8 and 9. The frontal, left side and right side conduits 7, 8 and 9 extend from the mask upper end, lower left side corner and lower right side corner 75, 76 and 77 respectively in flow communication with the airtight chamber 71 formed by the mask 13 to their distal ends 65 which are securable to the front, left side and right side tube connectors 60, 61 and 62 by interference or friction fit. The joining by friction fit connects both the secondary conduits 7, 8 and 9 and the straps 10, 11 and 12 to the airflow distributor 6.

A cross strap 80 is secured to and extends from the left side strap 11 to the right side strap 12 generally medially between the nasal mask 13 and the airflow distributor 6. The cross strap 80 is formed of elastic material and may be integrally formed with the left side and right side straps 11 and 12. The cross strap 80 may include fastening means (not shown) such as a buckle or the like for selectively connecting and disconnecting the connecting strap from between the left side and right side straps 11 and 12.

The headgear 16 is generally secured to the head of a wearer by pulling it over the wearer's head such that the nasal mask 13 encloses the wearer's nose and the left and right side straps 11 and 12 extend behind the wearer's left and right ears respectively as shown in FIG. 3. The straps are sized and positioned such that when the system is put on a wearer's head the airflow distributor 6 is generally positioned on top of the wearer's head.

In use, breathable gas, such as air, under a controlled pressure is directed from the pressurized air source 20 through the primary conduit 5 to the airflow distributor 6. The gas is then directed through the tube connectors 60, 61 and 62 and the secondary conduits 7, 8 and 9 to the airtight chamber 71 formed by the mask 13 where the gas is then directed through the nostrils of the wearer under pressure to provide continuous positive airway pressure to the user to help prevent obstructive sleep apnea.

The rotational or swivel connection of the primary conduit 5 to the airflow distributor 6 reduces stresses placed on the headgear 16, as the wearer moves their head during sleep. If during sleep, the wearer moves their head such that they are resting on one of the secondary conduits 7, 8 or 9 as shown in FIG. 1 and that secondary conduit 7, 8 or 9 becomes compressed or greatly restricted, pressurized gas will continue to be delivered to the airtight chamber 71 formed by the mask 13 from the other secondary conduits 7, 8 or 9.

The nasal mask 13 functions as airflow entrance means for directing airflow through the nostrils or nasal passages of a wearer. It is foreseen that the device could be adapted to use other airflow entrance means well known in the industry such as nasal pillows as shown in U.S. Pat. No. 4,782,832.

It is also foreseen that the secondary conduits 7, 8 and 9 could be formed separately from the straps 10, 11 and 12. The straps 10, 11 and 12 may be formed from materials such as elastic straps or rigid material including leather or synthetic resinous webbing and might further include length adjustment means. Such straps may be securable to the nasal mask 13 and airflow distributor through means such as adhesives or buckles and may incorporate quick release bayonet type buckles. The secondary conduits 7, 8 and 9 may run coextensively or separate from the straps 10, 11 and 12. Further the straps 10, 11 and 12 may include a sleeve through which respective secondary conduits 7, 8 and 9 might extend and be secured.

It is to be understood that while certain forms of the present invention have been illustrated and described herein, it is not to be limited to the specific forms or arrangement of parts described and shown.

What is claimed and desired to be secured by Letters Patent is as follows:

1. An airflow delivery system comprising:
   a. a first conduit adapted to be connected to a source of breathable air under pressure at a first end thereof;
   b. an airflow distributor connected to a secured end of said first conduit and connected in flow communication to at least two spaced secondary conduits; said delivery system being configured such that during use said airflow distributor is located near the top of the head of a user and at least two of said secondary conduits each extend along respective opposite sides of the head of the user; and
   c. said secondary conduits being connected in flow communication to an airflow entrance structure for directing airflow to the nostrils of a user.

2. The airflow delivery system as disclosed in claim 1 further comprising a plurality of straps connecting said airflow entrance structure to said airflow distributor and arranged to position said airflow distributor generally on top of the head of a user when said airflow entrance structure is positioned for directing airflow to the nostrils of a user.

3. The airflow delivery system as disclosed in claim 2 wherein each of said secondary conduits is secured to a respective one of said straps.

4. The air flow delivery system as described in claim 3 wherein each of said straps is positioned such that in operation each of said straps is substantially spaced on the head of user.

5. The airflow delivery system as disclosed in claim 2 wherein each of said secondary conduits is integrally formed with one of said straps.

6. The airflow delivery system as disclosed in claim 1 wherein said airflow entrance structure comprises a nasal mask.

7. The airflow delivery system as disclosed in claim 1 including a head encompassing unit for operably securing said airflow distributor near the top of the head of a user.

8. An airflow delivery system comprising:
   a. an air supply source for providing a source of breathable gas under a controlled pressure;
   b. a first conduit connected at a first end to said air supply source and rotatably connected at a second end to an airflow distributor;
   c. said airflow distributor connected in flow communication to at least one secondary conduit;
   d. said secondary conduit connected in flow communication to an airflow entrance structure for directing airflow into the nostrils of a user;
   e. a headgear mechanism for removably securing said airflow distributor to an upper portion of the head of a user.

9. The airflow delivery system as disclosed in claim 8 further comprising a plurality of straps connecting said airflow entrance structure to said airflow distributor and arranged to position said airflow distributor generally on top of the head of a user when said airflow entrance structure is positioned for directing airflow into the nostrils of a user.

10. The airflow delivery system as disclosed in claim 9 wherein each of said secondary conduits is secured to respective one of said straps.

11. The airflow delivery system as disclosed in claim 9 wherein each of said secondary conduits is integrally formed with a respective one of said straps.

12. The airflow delivery system as disclosed in claim 8 wherein said airflow entrance structure comprises a nasal mask.

13. An airflow delivery system comprising:
   a. an air supply source for providing a source of breathable gas under a controlled pressure;
   b. a first conduit connected at a first end to said air supply source and rotatably connected at a second end to an airflow distributor;
   c. said airflow distributor connected in flow communication to at least two secondary conduits; said airflow distributor being operably configured relative to a remainder of said system to be positioned near the top of a head of a user of the system during use thereof;

d. said secondary conduits connected in flow communication to an airflow entrance structure for directing airflow through the nostrils of a user;

e. a plurality of straps connecting said airflow entrance structure to said airflow distributor and arranged to operably position and extend from said airflow distributor located near the top of the head of a user with at least two of the straps each being located during use on respective opposite sides of the head of a user, when said airflow entrance structure is positioned for directing airflow into the nostrils of a user.

14. The airflow delivery system as disclosed in claim 13 wherein each of said secondary conduits is secured to a respective one of said straps.

15. The airflow delivery system as disclosed in claim 13 wherein each of said secondary conduits is integrally formed with a respective one of said straps.

16. An airflow delivery system comprising:

a. an air supply source for providing a source of breathable gas under a controlled pressure;

b. a first conduit connected at a first end to said air supply source and rotatably connected at a second end to an airflow distributor;

c. said airflow distributor connected in flow communication to at least two secondary conduits;

d. said secondary conduits connected in flow communication to an airflow entrance structure comprising a nasal mask for directing airflow through the nostrils of a user;

e. a plurality of straps connecting said airflow entrance structure to said airflow distributor and arranged to operably position said airflow distributor generally on top of the head of a user when said airflow entrance structure is positioned for directing airflow into the nostrils of a user; and f. said straps including a front strap secured to and extending from an upper end of said mask to said airflow distributor, a left side strap secured to and extending from a left side of said mask to said airflow distributor, and a right side strap secured to and extending from a right side of said mask to said airflow distributor.

17. The airflow delivery system as disclosed in claim 16 wherein said secondary conduits comprise:

a. a frontal conduit secured to said front strap;

b. a left side conduit secured to said left side strap; and c. a right side conduit secured to said right side strap.

18. An airflow delivery system comprising:

a. an air supply source for providing a source of breathable gas under a controlled pressure;

b. a first conduit connected at a first end to said air supply source and rotatably connected at a second end to an airflow distributor;

c. said airflow distributor connected in flow communication to a frontal conduit, a left side conduit and a right side conduit;

d. a nasal mask having an internal chamber and being sized and shaped to be operably positioned in enclosing relationship with the nose of a user for directing airflow into the nostrils of a user;

e. a front strap secured to and extending from an upper end of said mask to said airflow distributor, a left side strap secured to and extending from a left side of said mask to said airflow distributor and a right side strap secured to and extending from a right side of said mask to said airflow distributor; said straps sized and arranged to operably position said airflow distributor on top of the head of a user when said mask is secured in enclosing relationship with the nose of a user;

f. said frontal conduit secured to said front strap and connected to said nasal mask at an upper end thereof in flow communication with said mask internal chamber;

g. said left side conduit secured to said left side strap and connected to said nasal mask along a left side thereof in flow communication with said mask internal chamber; and h. said right side conduit secured to said right side strap and connected to said nasal mask along a right side thereof in flow communication with said mask internal chamber.

19. The airflow delivery system as disclosed in claim 18 wherein said frontal, left side and right side conduits are integrally formed in said front, left side and right side straps respectively.

20. The airflow delivery system as disclosed in claim 18 further comprising a cross strap secured to and extending between said left side and right side straps.

* * * * *